United States Patent
Zhang et al.

(10) Patent No.: US 11,767,565 B2
(45) Date of Patent: Sep. 26, 2023

(54) USE OF DETECTION REAGENT FOR DETECTING METHYLATION OF GENES ASSOCIATED WITH COLORECTAL CANCER, AND KIT

(71) Applicant: WUHAN AMMUNITION LIFE-TECH CO., LTD., Wuhan (CN)

(72) Inventors: Lianglu Zhang, Wuhan (CN); Tingting Li, Wuhan (CN); Lanlan Dong, Wuhan (CN); Zhicheng Wu, Wuhan (CN); Xihui Yao, Wuhan (CN); Yuzhu Chen, Wuhan (CN)

(73) Assignee: WUHAN AMMUNITION LIFE-TECH CO., LTD., Wuhan (CN)

( * ) Notice: Subject to any disclaimer, the term of this patent is extended or adjusted under 35 U.S.C. 154(b) by 0 days.

(21) Appl. No.: 17/628,385

(22) PCT Filed: May 29, 2020

(86) PCT No.: PCT/CN2020/093247
§ 371 (c)(1),
(2) Date: Jan. 19, 2022

(87) PCT Pub. No.: WO2021/012788
PCT Pub. Date: Jan. 28, 2021

(65) Prior Publication Data
US 2022/0267859 A1    Aug. 25, 2022

(30) Foreign Application Priority Data
Jul. 22, 2019  (CN) .......................... 201910661388.2

(51) Int. Cl.
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *C12Q 2600/154* (2013.01)

(58) Field of Classification Search
CPC .......................... C12Q 1/6886; C12Q 2600/154
See application file for complete search history.

(56) References Cited

U.S. PATENT DOCUMENTS

| | | | | |
|---|---|---|---|---|
| 2001/0053519 A1* | 12/2001 | Fodor | ............... | B82Y 30/00 |
| | | | | 536/24.1 |
| 2004/0241651 A1* | 12/2004 | Olek | ............... | C07K 14/4703 |
| | | | | 435/6.16 |
| 2016/0040244 A1* | 2/2016 | An | ............... | C12Q 1/6886 |
| | | | | 536/23.5 |
| 2016/0153050 A1 | 6/2016 | An et al. | | |
| 2017/0335405 A1* | 11/2017 | An | ............... | C12Q 1/6886 |

FOREIGN PATENT DOCUMENTS

| | | | | |
|---|---|---|---|---|
| CN | 103314114 A | | 9/2013 | |
| CN | 105112529 A | | 12/2015 | |
| CN | 106893777 A | | 6/2017 | |
| CN | 108103195 A | | 6/2018 | |
| CN | 109486955 A | * | 3/2019 | ........... C12Q 1/6886 |
| CN | 110343764 A | | 10/2019 | |
| CN | 108103195 B | | 8/2021 | |
| CN | 108707667 B | | 10/2021 | |
| WO | WO-2008084219 A1 | * | 7/2008 | ............. A61P 35/04 |
| WO | 2014062218 A1 | | 4/2014 | |
| WO | WO-2018087129 A1 | * | 5/2018 | |
| WO | 2018195211 A1 | | 10/2018 | |
| WO | 2018211404 A1 | | 11/2018 | |

OTHER PUBLICATIONS

Bartak et al. Epigenetics. 2017. 12(9):751-763. (Year: 2017).*
Rasmussen et al. Plos One. 2017. 12(7):e0180809. (Year: 2017).*
Chinese Application No. 2019106613882, First Office Action (with English translation).
Chinese Application No. 2019106613882, Notification to Grant Patent Right (with English translation).
Chinese Application No. 2019106613882, Second Office Action (with English translation).
International Search Report for International Application No. WO2021012788 (with English translation).
European Office Action dated May 31, 2022 for European Patent Application No. 20 827 996.8, 4 pages.

* cited by examiner

*Primary Examiner* — Joseph G. Dauner

(57) ABSTRACT

Provided are the use of a detection reagent for detecting the methylation of genes associated with colorectal cancer, and a kit. The kit comprises the detection reagent for detecting the methylation of genes associated with colorectal cancer.

3 Claims, 2 Drawing Sheets

Specification includes a Sequence Listing.

USE OF DETECTION REAGENT FOR DETECTING METHYLATION OF GENES ASSOCIATED WITH COLORECTAL CANCER, AND KIT

CROSS-REFERENCE TO RELATED APPLICATIONS

The present disclosure claims the priority of the Chinese Patent Application No. 201910661388.2, entitled "Use of Detection Reagent for Detecting Methylation of Genes Associated with Colorectal Cancer, and Kit", filed with the Chinese Patent Office on Jul. 22, 2019, the entity of which is incorporated herein by reference.

REFERENCE TO AN ELECTRONIC SEQUENCE LISTING

The contents of the electronic sequence listing (20220920_01799_US_Sequence_Listing.txt; Size: 9,883 bytes; and Date of Creation: Sep. 20, 2022) is herein incorporated by reference in its entirety.

TECHNICAL FIELD

The present disclosure pertains to the technical field of genetic detection, and particularly to uses and a kit of a detection reagent for detecting methylation of colorectal cancer-related genes (i.e., use of a detection reagent for detecting methylation of genes associated with colorectal cancer, and a kit).

BACKGROUND

Colorectal cancer is the third severest malignant tumor in the world. In recent years, the incidence of colorectal cancer in China has been increasing year by year, and it is estimated that there are about 400,000 new cases each year, ranking second among malignant tumors of the digestive system in our country. Colorectal cancer is usually developed slowly from precancerous polyps through a series of changes in genetics, especially in epigenetics, and through histological and morphological changes. Most colorectal tumors grow slowly, remain silent or asymptomatic, until they reach a certain size or developmental stage. Therefore, colorectal cancer can be found through screening and accordingly intervened. The 5-year survival rate after surgery of patients with early-stage colorectal cancer can reach up to over 90%, and the 5-year survival rate of patients in mid-term and advanced stage is only about 10%, while about 80% of clinically diagnosed cases of colorectal cancer are in the mid-term and advanced stage, which is one of key factors leading to a stubbornly high mortality rate. Through early and effective treatment, the incidence of colorectal cancer in patients is reduced by 60%, and the mortality rate is reduced by 80%. Therefore, the early detection, early diagnosis, and early treatment of colorectal cancer are particularly important.

The formation mechanism of colorectal cancer is very complicated, of which the cancerating process is the result of multi-step, multi-pathway and multi-gene participation. Mutations of proto-oncogenes and tumor suppressor genes, as well as changes in signal pathway molecules such as methylation, proliferation and apoptosis, all play an important role in the induction and development of colorectal cancer.

Colonoscopy is the gold standard for the detection and definite diagnosis of colorectal cancer. However, because it requires a complicated bowel preparation process, has certain invasiveness, and requires professional technicians, its popularity among the general population is not high. Non-invasive detection methods such as fecal occult blood test (FOBT) and fecal immunochemical test (FIT) are not very sensitive, especially have relatively low sensitivity in the aspect of detection of stage I colorectal cancer and advanced adenoma. Therefore, for the detection of colorectal cancer and precancerous lesions, a highly sensitive and specific non-invasive detection method is urgently needed.

Methylation is an epigenetic modification, and its abnormal changes may cause changes in DNA conformation and the mode of interactions between DNA and proteins etc., and accordingly control gene expression. DNA methylation plays an important role in aspects of regulation of gene expression, cell proliferation and differentiation, growth, and gene imprinting etc., and is closely related to the formation/occurrence and the progression of tumors. More and more studies have shown that abnormal DNA methylation is an early event of cancer induction, and there are changes in the level and pattern of DNA methylation during the induction/occurrence and development of colorectal cancer. Finding specific methylated segments plays a decisive role in the early detection of colorectal cancer. However, existing colorectal cancer-related methylation detection technologies have prominent problems of complicated operation steps, low detection sensitivity and the like.

SUMMARY

An object of the present disclosure comprises: e.g. providing uses and a kit of a detection reagent for detecting methylation of colorectal cancer-related genes, and providing a method for auxiliary diagnosis of colorectal cancer. As for the kit and the method according to the present disclosure, the sensitivity and the specificity of the detection can be significantly improved by using different detection regions of same or different colorectal cancer-related genes as detection target region of methylation, so as to realize the purpose of early, rapid and accurate detection of colorectal cancer and colorectal adenoma.

The present disclosure is implemented in following manner:

An embodiment of the present disclosure provides the use of a detection reagent in the preparation of a kit for auxiliary diagnosis of colorectal cancer, with detection reagent detecting methylation of colorectal cancer-related genes, wherein the colorectal cancer-related gene mentioned above is one selected from SDC2 gene, TFPI2 gene and a combination of the two; the detection reagent mentioned above contains a first reagent for detecting methylation of a first target region on the SDC2 gene or/and a second reagent for detecting methylation of a second target region on the TFPI2 gene, wherein the first target region mentioned above is any one selected from following regions of the SDC2 gene; or a combination of at least two thereof:

region a, region b, and region c;

wherein the region a is selected from the full-length region and partial region of chr8:96493351-96493635, the region b is selected from the full-length region and partial region of chr8:96493701-96493935, and the region c is selected from the full-length region and partial region of chr8:96494006-96494335;

the second target region mentioned above is any one selected from following regions of the TFPI2 gene: region d and region e; or a combination thereof,
wherein the region d is selected from the full-length region and partial region of chr7:93890026-93890319, and the region e is selected from the full-length region and partial region of chr7:93890630-93890991.

The present disclosure provides the use of a detection reagent in the auxiliary diagnosis of colorectal cancer, with the detection reagent detecting methylation of colorectal cancer-related genes, characterized in that the colorectal cancer-related gene is one selected from SDC2 gene, TFPI2 gene and a combination of the two; the detection reagent contains a first reagent for detecting methylation of a first target region on the SDC2 gene or/and a second reagent for detecting methylation of a second target region on the TFPI2 gene;
  wherein the first target region is any one selected from following regions of the SDC2 gene: region a, region b, and region c; or a combination of at least two thereof;
  wherein the region a is selected from the full-length region and partial region of chr8:96493351-96493635, the region b is selected from the full-length region and partial region of chr8:96493701-96493935, and the region c is selected from the full-length region and partial region of chr8:96494006-96494335;
  the second target region is any one selected from following regions of the TFPI2 gene: region d and region e; or a combination thereof;
  wherein the region d is selected from the full-length region and partial region of chr7:93890026-93890319, and the region e is selected from the full-length region and partial region of chr7:93890630-93890991.

The present disclosure provides a method for auxiliary diagnosis of colorectal cancer in a subject, comprising the following steps:
  detecting methylation of colorectal cancer-related genes in a sample from the subject, and
  analyzing the methylation of colorectal cancer-related genes in the sample from the subject,
  wherein the colorectal cancer-related gene is one selected from SDC2 gene, TFPI2 gene and a combination of the two, and the methylation of the colorectal cancer-related genes comprises methylation of a first target region on the SDC2 gene or/and methylation of a second target region;
  the first target region is any one selected from following regions of the SDC2 gene: region a, region b, and region c; or a combination of at least two thereof;
  the region a is selected from the full-length region and partial region of chr8:96493351-96493635, the region b is selected from the full-length region and partial region of chr8:96493701-96493935, and the region c is selected from the full-length region and partial region of chr8:96494006-96494335;
  the second target region is any one selected from following regions of the TFPI2 gene: region d and region e; or a combination thereof;
  the region d is selected from the full-length region and partial region of chr7:93890026-93890319, and the region e is selected from the full-length region and partial region of chr7:93890630-93890991.

It is discovered in the research of the present disclosure that the sensitivity and the specificity of the detection are closely related to the detection region of the target gene. This is mainly because in an entire relatively longer gene and its regulatory sequence, the differentially methylated region (DMR) only occupies a small part, and only when this small part of DMR is specifically detected, samples can be better discriminated from each other, hereby greatly improving detection sensitivity and specificity.

It is discovered in the research of the present disclosure that when colorectal cancer-related gene such as SDC2 gene or TFPI2 gene is used as detection target gene for auxiliary diagnosis of colorectal cancer or precancerous lesions, the sensitivity and the specificity of auxiliary diagnosis of colorectal cancer can be significantly improved, no matter whether any one or a combination of several from the full-length region or partial region of chr8:96493351-96493635, the full-length region or partial region of chr8:96493701-96493935, and the full-length region or partial region of chr8:96494006-96494335 on the SDC2 gene is selected as the target region for methylation detection, or any one or a combination of the two from the full-length region or partial region of chr7:93890026-93890319 and the full-length region or partial region of chr7:93890630-93890991 on the TFPI2 gene is selected as the target region for methylation detection, or a combination of the above target region selected from the SDC2 gene and the above target region selected from the TFPI2 gene is used as the target region for methylation detection, and more accurate and reliable reference can be provided accordingly for early screening and diagnosis of colorectal cancer or colorectal adenoma.

The location of the SDC2 gene is: chromosome 8, NC_000008.11 (96493601-96611790), and the promoter region is generally situated upstream of the transcription start site.

The location of the TFPI2 gene is: chromosome 7, NC_000007.14 (93885396-93890753, complementary), and the promoter region is generally situated upstream of the transcription start site.

In one or more embodiments, the region a mentioned above is selected from the full-length region and partial region of chr8:96493393-96493629.

In one or more embodiments, the region b mentioned above is selected from the full-length region and partial region of chr8:96493701-96493900.

In one or more embodiments, the region c mentioned above is selected from the full-length region and partial region of chr8:96494006-96494327.

In one or more embodiments, the region a mentioned above is selected from either one of chr8:96493393-96493581 and chr8:96493456-96493629.

In one or more embodiments, the region b mentioned above is selected from either one of chr8:96493701-96493858 and 96493770-96493900.

In one or more embodiments, the region c mentioned above is selected from either one of chr8:96494006-96494166 and chr8:96494140-96494327.

In one or more embodiments, the region a mentioned above is selected from chr8:96493456-96493581.

In one or more embodiments, the region b mentioned above is selected from 96493770-96493858.

In one or more embodiments, the region c mentioned above is selected from chr8:96494140-96494166.

In one or more embodiments, the region d mentioned above is selected from the full-length region and partial region of chr7:93890026-93890312.

In one or more embodiments, the region e mentioned above is selected from the full-length region and partial region of chr7:93890651-93890976.

In one or more embodiments, the region d mentioned above is selected from either one of chr7:93890026-93890176 and chr7:93890149-93890312.

In one or more embodiments, the region e mentioned above is selected from either one of chr7:93890651-93890825 and chr7:93890807-93890976.

In one or more embodiments, the region d mentioned above is selected from chr7:93890149-93890176.

In one or more embodiments, the region e mentioned above is selected from chr7:93890807-93890825.

In one or more embodiments, the step of detecting methylation of colorectal cancer-related genes in a sample from the subject is performed using a detection reagent, the detection reagent contains a first reagent for detecting methylation of a first target region on the SDC2 gene or/and a second reagent for detecting methylation of a second target region on the TFPI2 gene.

In one or more embodiments, the step of detecting methylation of colorectal cancer-related genes in a sample from the subject refers to the detection of methylation of any two from the following: the region a of the SDC2 gene, the region b of the SDC2 gene, the region c of the SDC2 gene, the region d of the TFPI2 gene, and the region e of the TFPI2 gene, and the analyzing step (i.e. analyzing methylation of colorectal cancer-related genes in the sample from the subject) refers to the analysis of a combination of the methylation results of the any two.

In one or more embodiments, the first reagent and/or the second reagent contains one or more of the following elements: primers, probes, sulfites, sample preservation solutions, nucleic acid extraction solutions, PCR reaction liquids, positive control, negative control, endogenous reference, and standard reagents.

Generally, methods for detecting DNA methylation include, but are not limited to, methylation detection methods based on sulfites (and/or bisulfites), such as methylation-specific PCR, sequencing, and high-resolution melting; and direct genomic sequencing. A person skilled in the art could select a method for detecting DNA methylation as needed, and detection reagents or kits used in these methods all fall within the scope of the present disclosure.

In one or more embodiments, the colorectal cancer-related gene as mentioned above is a union from the SDC2 gene and the TFPI2 gene; the above detection reagent comprises a first reagent for detecting methylation of a first target region on the SDC2 gene and a second reagent for detecting methylation of a second target region on the TFPI2 gene;
the first target region mentioned above is the region c; and the second target region mentioned above is the region d.

It is further discovered in the research of the present disclosure that the sensitivity, the specificity and AUC of the detection results can be apparently improved by uniting the SDC2 gene and the TFPI2 gene, i.e. uniting the region c selected from the SDC2 gene and the region d selected from the TFPI2 gene, and using the methylation results of the two regions as determination basis for auxiliary diagnosis of colorectal cancer.

In one or more embodiments, the first reagent mentioned above contains a first nucleic acid group for detecting methylation of the first target region mentioned above, and the first nucleic acid group mentioned above contains the combination of a fluorescent probe c and a primer pair c or the combination of a fluorescent probe c1 and a primer pair c1;

the second reagent mentioned above contains a second nucleic acid group for detecting methylation of the second target region mentioned above, and the second nucleic acid group mentioned above contains the combination of a primer pair d and a fluorescent probe d or the combination of a primer pair d1 and a fluorescent probe d1;

wherein the base sequence of the primer pair c mentioned above is shown in SEQ ID NOs: 11-12, and the base sequence of the fluorescent probe c mentioned above is shown in SEQ ID NO: 13; the base sequence of the primer pair c1 mentioned above is shown in SEQ ID NOs: 14-15, and the base sequence of the fluorescent probe c1 mentioned above is shown in SEQ ID NO: 16;

the base sequence of the primer pair d mentioned above is shown in SEQ ID NOs: 17-18, and the base sequence of the fluorescent probe d mentioned above is shown in SEQ ID NO: 19; the base sequence of the primer pair d1 mentioned above is shown in SEQ ID NOs: 20-21, and the base sequence of the fluorescent probe d1 mentioned above is shown in SEQ ID NO: 22.

It shall be clarified that according to the contents of the present disclosure, a person skilled in the art could readily design a variety of primer pairs and probes directed at methylation of the above target regions, and they all fall within the scope of protection of the present disclosure, no matter which primer pairs and probes are used, which are not limited to above primer pairs and probes in the present disclosure, as long as they can diagnose colorectal cancer or assist in its diagnosis by detecting all segments or partial segments of any target region as mentioned above.

In one or more embodiments, the 5' end of each fluorescent probe mentioned above is labeled with a fluorescent group, and the 3' end of the probe mentioned above is labeled with a quenching group.

In one or more embodiments, the fluorescent group is any one selected from the group consisting of FAM™, VIC®, TET™, JOE™, HEX™, CY®3, CY®5, ROX™, RED610, TEXAS RED®, TAMRA™, RED670 and NED™, and the quenching group mentioned above is any one selected from the group consisting of BHQ®-1, BHQ®-2, BHQ®-3 and Minor Groove Binder Nonfluorescent Quencher (MGB NFQ).

In one or more embodiments, the detection sample of the above kit is a blood sample, a colorectal tissue sample or a stool sample taken from a subject to be detected.

In one or more embodiments, the auxiliary diagnosis of colorectal cancer comprises:
discriminating colorectal cancer and/or colorectal adenoma from normal tissues;
performing auxiliary diagnosis of early colorectal cancer; and/or
assessing the risk of being affected with colorectal cancer.

The present disclosure provides a kit for auxiliary diagnosis of colorectal cancer, which comprises a detection reagent for detecting methylation of a colorectal cancer-related gene; the colorectal cancer-related gene mentioned above is one selected from SDC2 gene, TFPI2 gene and a combination of the two; the detection reagent mentioned above contains a first reagent for detecting methylation of a first target region on the SDC2 gene or/and a second reagent for detecting methylation of a second target region on the TFPI2 gene;
wherein the first target region mentioned above is any one selected from following regions of the SDC2 gene: region a, region b, and region c; or a combination of at least two thereof;

wherein the region a is selected from the full-length region and partial region of chr8:96493351-96493635, the region b is selected from the full-length region and partial region of chr8:96493701-96493935, and the region c is selected from the full-length region and partial region of chr8:96494006-96494335;

the second target region mentioned above is any one selected from following regions of the TFPI2 gene: region d and region e; or a combination thereof;

wherein the region d is selected from the full-length region and partial region of chr7:93890026-93890319, and the region e is selected from the full-length region and partial region of chr7:93890630-93890991.

In one or more embodiments, the region a mentioned above is selected from the full-length region and partial region of chr8:96493393-96493629.

In one or more embodiments, the region b mentioned above is selected from the full-length region and partial region of chr8:96493701-96493900.

In one or more embodiments, the region c mentioned above is selected from the full-length region and partial region of chr8:96494006-96494327.

In one or more embodiments, the region a mentioned above is selected from any one of chr8:96493393-96493581 and chr8:96493456-96493629.

In one or more embodiments, the region b mentioned above is selected from any one of chr8:96493701-96493858 and 96493770-96493900.

In one or more embodiments, the region c mentioned above is selected from any one of chr8: 96494006-96494166 and chr8: 96494140-96494327.

In one or more embodiments, the region a mentioned above is selected from chr8:96493456-96493581.

In one or more embodiments, the region b mentioned above is selected from 96493770-96493858.

In one or more embodiments, the region c mentioned above is selected from chr8:96494140-96494166.

In one or more embodiments, the region d mentioned above is selected from the full-length region and partial region of chr7:93890026-93890312.

In one or more embodiments, the region e mentioned above is selected from the full-length region and partial region of chr7:93890651-93890976.

In one or more embodiments, the region d mentioned above is selected from chr7:93890026-93890176 and chr7: 93890149-93890312.

In one or more embodiments, the region e mentioned above is selected from chr7:93890651-93890825 and chr7: 93890807-93890976.

In one or more embodiments, the region d mentioned above is selected from chr7:93890149-93890176.

In one or more embodiments, the region e mentioned above is selected from chr7:93890807-93890825.

In one or more embodiments, the colorectal cancer-related gene as mentioned above is a union from the SDC2 gene and the TFPI2 gene; the above detection reagent contains a first reagent for detecting methylation of a first target region on the SDC2 gene and a second reagent for detecting methylation of a second target region on the TFPI2 gene;

the first target region mentioned above is the region c; and the second target region mentioned above is the region d.

In one or more embodiments, the first reagent mentioned above contains a first nucleic acid group for detecting methylation of the first target region mentioned above, and the first nucleic acid group mentioned above contains the combination of a fluorescent probe c and a primer pair c or the combination of a fluorescent probe c1 and a primer pair c1.

The second reagent mentioned above contains a second nucleic acid group for detecting methylation of the second target region mentioned above, and the second nucleic acid group mentioned above contains the combination of a primer pair d and a fluorescent probe d or the combination of a primer pair d1 and a fluorescent probe d1.

In the above, the base sequence of the primer pair c mentioned above is shown in SEQ ID NOs: 11-12, and the base sequence of the fluorescent probe c mentioned above is shown in SEQ ID NO: 13; and the base sequence of the primer pair c1 mentioned above is shown in SEQ ID NOs: 14-15, and the base sequence of the fluorescent probe c1 mentioned above is shown in SEQ ID NO: 16.

The base sequence of the primer pair d mentioned above is shown in SEQ ID NOs: 17-18, and the base sequence of the fluorescent probe d mentioned above is shown in SEQ ID NO: 19; and the base sequence of the primer pair d1 mentioned above is shown in SEQ ID NOs: 20-21, and the base sequence of the fluorescent probe d1 mentioned above is shown in SEQ ID NO: 22.

Preferably, the detection sample of the above kit is a blood sample, a colorectal tissue sample or a stool sample taken from a subject to be detected.

In one or more embodiments, in addition to the reagents mentioned above, the above kit further contains one or more from sample preservation solutions, nucleic acid extraction solutions, PCR reaction liquids, positive control, negative control, endogenous reference, and standard reagents.

In one or more embodiments, the kit for auxiliary diagnosis of colorectal cancer further contains one or more of the following elements: sulfites, sample preservation solutions, nucleic acid extraction solutions, PCR reaction liquids, positive control, negative control, endogenous reference, and standard reagents.

In one or more embodiments, the auxiliary diagnosis of colorectal cancer comprises:
discriminating colorectal cancer and/or colorectal adenoma from normal tissues;
performing auxiliary diagnosis of early colorectal cancer; and/or
assessing the risk of being affected with colorectal cancer.

The present disclosure has beneficial effects as follows:

Through the kit for auxiliary diagnosis of colorectal cancer provided in the present disclosure, the auxiliary diagnosis of colorectal cancer is enabled to have better sensitivity and specificity and provide more accurate, reliable reference for early screening, diagnosis and the like of colorectal cancer or colorectal adenoma, by performing methylation detection on specific regions in the SDC2 gene and/or the TFPI2 gene (e.g. separately detecting chr8: 96493351-96493635, chr8:96493701-96493935 and chr8: 96494006-96494335 of the SDC2 gene, or detecting a combination of these regions; and e.g. separately detecting chr7:93890026-93890319 or chr7: 93890630-93890991 of the TFPI2 gene, or a combination of the two regions; e.g. detecting a combination of the SDC2 gene and the TFPI2 gene) and using the methylation detection results of these regions, especially united detection results as basis for auxiliary diagnosis of colorectal cancer.

BRIEF DESCRIPTION OF THE DRAWINGS

In order to more clearly describe the technical solutions of the embodiments of the present disclosure, the figures required to be used in the embodiments will be briefly introduced below; and it should be understood that the following figures merely show certain embodiments of the present disclosure, and thus should not be deemed as limiting the scope, and for a person ordinarily skilled in the art, other relevant figures could be obtained according to these figures without inventive efforts.

DETAILED DESCRIPTION OF THE EMBODIMENTS

Figure 1:
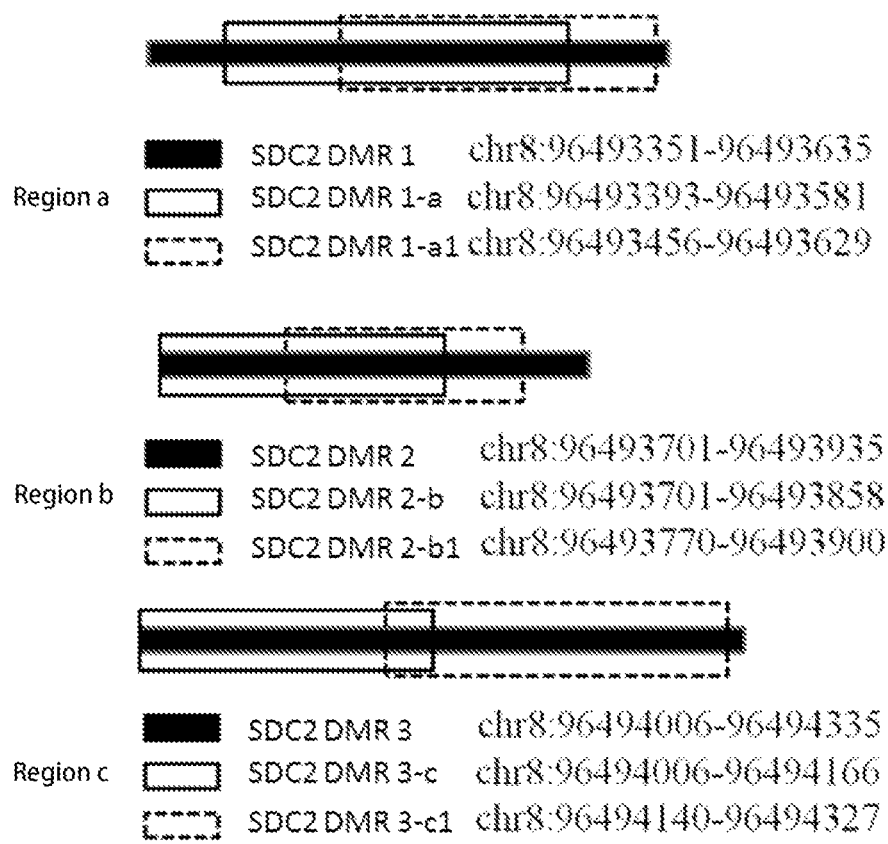
FIG. 1 is a schematic diagram showing the positional relationships of respective target regions of SDC2 gene in an embodiment of the present disclosure.

In order to make the objects, the technical solutions and the advantages of the embodiments of the present disclosure clearer, the technical solutions in the embodiments of the present disclosure will be clearly and comprehensively described below. Examples, for which no concrete conditions are specified, are performed according to conventional conditions or conditions recommended by the manufactures. Reagents or instruments that are used, for which no manufacturers are specified, are conventional products available commercially.

The features and the performance of the present disclosure will be further described in detail below with reference to the embodiments.

As used herein, the terms "base sequence" and "nucleotide sequence" may be used interchangeably, and generally refer to the sequence of basic groups in DNA or RNA.

As used herein, the term "diagnosis" or "auxiliary diagnosis" refers to making a judgment about people's mental and physical state from the medical point of view. Specifically, it refers to a process of determining which disease or condition can explain the symptoms and signs of a subject. For example, it is determined whether the subject suffers from colorectal cancer by using the target region of the colorectal cancer-related gene described herein as target spot. "Diagnosis" or "auxiliary diagnosis" may be a process independently used for making a definite diagnosis of colorectal cancer, or may be a process used in combination with other diagnostic techniques for making a definite diagnosis of colorectal cancer. "Diagnosis" or "auxiliary diagnosis" includes, but is not limited to, making a definite diagnosis of colorectal cancer or precancerous lesions of colorectal cancer, especially colorectal adenoma, and determining the risk of developing into colorectal cancer.

The term "primer" refers to a natural or synthetic oligonucleotide that, after forming a duplex with a polynucleotide template, can act as the start point for nucleic acid synthesis and extend from its 3' end along the template, hereby forming an expanded duplex. The nucleotide sequence added during the extending process is determined by the sequence of the template polynucleotide. Primers are usually extended by DNA polymerase. A primer usually has a length compatible with its use in the synthesis of the extension product of the primer, and its specific length is influenced by many factors, such as the temperature, the primer source, and the experimental method.

The term "probe" refers to an oligonucleotide that is able to be selectively hybridized with an amplified target nucleic acid under suitable conditions. In the kinetic PCR formulation, the detection probe can be composed of an oligonucleotide having a 5' reporter dye (R) and a 3' quenching dye (Q).

A person skilled in the art could design primers and probes other than that described in the present disclosure according to the target nucleotide sequence described in the present disclosure, which also fall within the scope of the present disclosure.

Terms "subject", "individual", and "patient" are used interchangeably herein, and refer to vertebrates, preferably mammals, most preferably human beings.

Mammals include, but are not limited to, murine, apes, human beings, domestic animals, sports animals, and pets.

Example 1

The present example provides a kit for auxiliary diagnosis of colorectal cancer or colorectal adenoma, comprising: a detection reagent for detecting methylation of a colorectal cancer-related gene, wherein the colorectal cancer-related gene is SDC2 gene, and the detection reagent contains a first reagent for detecting methylation of a first target region on the SDC2 gene;

The first target region is any one selected from following regions of the SDC2 gene: region a, region b, and region c;

In the above, referring to FIG. 1, the region a is selected from the full-length region of chr8:96493351-96493635 (hereinafter referred to as SDC2 DMR1 for short, and it shall be clarified that in other examples, the region a may be selected from the partial region of chr8:96493351-96493635, wherein it falls within the scope of protection of the present disclosure, no matter whether the full length or partial region from chr8:96493351-96493635 is detected);

The region b is selected from the full-length region of chr8:96493701-96493935 (hereinafter referred to as SDC2 DMR2 for short, and it shall be clarified that in other examples, the region b may be selected from the partial region of chr8:96493701-96493935, wherein it falls within the scope of protection of the present disclosure, no matter whether the full length or partial region from chr8:96493701-96493935 is detected);

The region c is selected from the full-length region of chr8:96494006-96494335 (hereinafter referred to as SDC2 DMR3 for short, and it shall be clarified that in other examples, the region c may be selected from the partial region of chr8:96494006-96494335, wherein it falls within the scope of protection of the present disclosure, no matter whether the full length or partial region from chr8:96494006-96494335 is detected).

The base sequence of one DNA single strand in the full-length target region of SDC2 DMR1 is as follows (as set forth in SEQ ID NO: 29):

AGAAAAGCTACATACGTCTCTCGTTTCTTCACTAATTGTTCTCTAGAAA

AGGGAAAGTGAAGAAGGGAAAGAGAAAAGACAACGGGGAAGAAAAGAG

CATAGAGGAGAGAGGAAAAGTGGGGAGAGAAAGGAAGAAAAGGACTGA

GAAAACGCAGGAGCCCTGGCTTGCCGGTGAGCAGAGCCGGCGCAGCC

ACAGCGCGGAGCCGCGGCGCCCACTGGTCCTCGGAGCTGCCAATCGG

CGTGTAATCCTGTAGGAATTTCTCCCGGGTTTATCTGGGAGTCACA;

The base sequence of one DNA single strand in the full-length target region of SDC2 DMR2 is as follows (as set forth in SEQ ID NO: 30):

AGAGGAAAAGAAGAGGAGGAGAAGGAGGAGGACCCGGGGAGGGAG

GCGCGGCGCGGGAGGAGGAGGGGCGCAGCCGCGGAGCCAGTGGCCC

CGCTTGGACGCGCTGCTCTCCAGATACCCCCGGAGCTCCAGCCGCGCG

GATCGCGCGCTCCCGCCGCTCTGCCCCTAAACTTCTGCCGTAGCTCCCT

TTCAAGCCAGCGAATTTATTCCTTAAAACCAGAAACTGAACCTCGGC;

The base sequence of one DNA single strand in the full-length target region of SDC2 DMR3 is as follows (as set forth in SEQ ID NO: 31):

GAGCACCAACTCCGTGTCGGGAGTGCAGAAACCAACAAGTGAGAGGG

CGCCGCGTTCCCGGGGCGCAGCTGCGGGCGGCGGGAGCAGGCGCAG

GAGGAGGAAGCGAGCGCCCCCGAGCCCCGAGCCCGAGTCCCCGAGCC

TGAGCCGCAATCGCTGCGGTACTCTGCTCCGGATTCGTGTGCGCGGGC

TGCGCCGAGCGCTGGGCAGGAGGCTTCGTTTTGCCCTGGTTGCAAGCA

GCGGCTGGGAGCAGCCGGTCCCTGGGGAATATGCGGCGCGCGTGGAT

CCTGCTCACCTTGGGCTTGGTGGCCTGCGTGTCGGCGGAGTCGGTGA.

The detection reagent used in the present example for detecting the above target regions is any reagent in the art capable of realizing the methylation detection of the above target regions.

Example 2

The kit for auxiliary diagnosis of colorectal cancer or colorectal adenoma provided in the present example is substantially the same as that in example 1, except that in the present example:

the region a is selected from partial region of SDC2 DMR1, specifically, referring to FIG. 1, the region a is selected from chr8:96493393-96493581 (named as SDC2 DMR 1-a) and chr8:96493456-96493629 (named as SDC2 DMR 1-a1);

the region b is selected from partial region of SDC2 DMR2, specifically, referring to FIG. 1, the region b is selected from chr8:96493701-96493858 (named as SDC2 DMR 2-b) and 96493770-96493900 (named as SDC2 DMR 2-b1); and the region c is selected from partial region of SDC2 DMR3, specifically, referring to FIG. 1, the region c is selected from chr8:96494006-96494166 (named as SDC2 DMR 3-c) and chr8:96494140-96494327 (named as SDC2 DMR 3-c1).

Further, the kit of the present example further contains a primer pair and a fluorescent probe for detecting respective target regions as mentioned above, and the specific nucleotide sequences are shown in Table 1.

TABLE 1

Sequences of primer pairs and probes used in the example of the present disclosure for detecting respective target regions

| Primer Name | Direction | Sequence (5'-3') | Target Region | SEQ ID NO.: |
|---|---|---|---|---|
| Primer pair a | Forward | TTAGAAAAGGGAAAG TGAAGAAGGG | SDC2 DMR 1-a | 1 |
|  | Reverse | CAACTCCGAAAACCA ATAAACG |  | 2 |
| Primer pair a1 | Forward | AGAGAGGAAAAGTGG GGAGAGAAAG | SDC2 DMR 1-a1 | 3 |
|  | Reverse | TCCCAAATAAACCCGA AAAAATTC |  | 4 |
| Probe a | / | CTATAACTACGCCGAC TCTACTCACC | used in combination with the primer pair a or the primer pair a1 | 5 |
| Primer pair b | Forward | AGAGGAAAAGAAGAG GAGGAGAAGG | SDC2 DMR 2-b | 6 |
|  | Reverse | ACGACGAAAACGCGC GATC |  | 7 |
| Primer pair b1 | Forward | GTAGTCGCGGAGTTA GTGGTTT | SDC2 DMR 2-b1 | 8 |
|  | Reverse | CGCTAACTTAAAAAAA AACTACGAC |  | 9 |
| Probe b | / | ATCTAAAAACAACGC GTCC | used in combination with the primer pair b or the primer pair b1 | 10 |
| Primer pair c | Forward | GAGTATTAATTTCGTG TCGGGAGTG | SDC2 DMR 3-c | 11 |
|  | Reverse | TACCGCAACGATTACG ACTCAAAC |  | 12 |
| Probe c | / | CAACTACGCCCCGAA AA CGC | used in combination with the primer pair c | 13 |

TABLE 1-continued

Sequences of primer pairs and probes used in the example
of the present disclosure for detecting respective target regions

| Primer Name | Direction | Sequence (5'-3') | Target Region | SEQ ID NO.: |
|---|---|---|---|---|
| Primer pair c1 | Forward | CGAGTTTGAGTCGTAA TCGTTGC | SDC2 DMR 3-c1 | 14 |
|  | Reverse | TCCGCCGACACGCAA ACCACCAAACC |  | 15 |
| Probe c1 | / | AACAAAACGAAACCT CCTACCCAAC | used in combination with the primer pair c1 | 16 |
| Primer pair d | Forward | ATTTGGGAGGTTTGC GACGAT | TFPI2 DMR1-d | 17 |
|  | Reverse | AAACCCAAACTAAAAC TTCC |  | 18 |
| Probe d | / | CGAAAATCCTAAATAC GCGCAAAAC | used in combination with the primer pair d | 19 |
| Primer pair d1 | Forward | CGCGGAGATTTGTTTT TTGT | TFPI 2 DMR 1-d1 | 20 |
|  | Reverse | AACAAACATCGTCGC AAACCTC |  | 21 |
| Probe d1 | / | ATAAAACCCGACAAAA TCCG | used in combination with the primer pair d1 | 22 |
| Primer pair e | Forward | TTAGGTTTCGTTTCGG CGG | TFPI2 DMR2-e | 23 |
|  | Reverse | ACAACCCCAAAAAAC GAACGAAATC |  | 24 |
| Probe e | / | TCTACTCCAAACGAC CCGAATACC | used in combination with the primer pair e | 25 |
| Primer pair e1 | Forward | GTTTTTTTAGGGCGTT TTCGTTTGG | TFPI2 DMR2-e1 | 26 |
|  | Reverse | CCGCCGAAACGAAAC CTAAAA |  | 27 |
| Probe e1 | / | TTCATACACGAAAACT ATCACCCCG | used in combination with the primer pair e1 | 28 |

Example 3

The present example provides a kit for auxiliary diagnosis of colorectal cancer or colorectal adenoma, comprising: a detection reagent for detecting methylation of a colorectal cancer-related gene, wherein the colorectal cancer-related gene is TFPI2 gene, and the detection reagent contains a second reagent for detecting methylation of a second target region on the TFPI2 gene.

In the above, the second target region is any one selected from following regions of the TFPI2 gene: region d and region e.

In the above, referring to FIG. 2, the region d is selected from the full-length region of chr7:93890026-93890319 (hereinafter referred to as TFPI2 DMR1 for short, and it shall be clarified that in other examples, the region d may be selected from the partial region of TFPI2 DMR1, wherein it falls within the scope of protection of the present disclosure, no matter whether the full length or partial region from chr7:93890026-93890319 is detected);

The region e is selected from the full-length region of chr7:93890630-93890991 (hereinafter referred to as TFPI2 DMR2 for short, and it shall be clarified that in other examples, the region e may be selected from the partial region of TFPI2 DMR2, wherein it falls within the scope of protection of the present disclosure, no matter whether the full length or partial region from the region chr7:93890630-93890991 is detected).

In the above, the base sequence of one DNA single strand in the full-length target region of TFPI2 DMR1 is as follows (as set forth in SEQ ID NO: 32):

GAAATAACGCGGAGATCTGTCTCCTGCCCCTAGACTACGGACCCTGC

CGGGCCCTACTTCTCCGTTACTACTACGACAGGTACACGCAGAGCTGCC

GCCAGTTCCTGTACGGGGGCTGCGAGGGCAACGCCAACAATTTCTACAC

CTGGGAGGCTTGCGACGATGCTTGCTGGAGGATAGAAAGTAAGTGCCCT

GCGCGCACCCAGGACTCTCGCGCTCCTTGCGCCGGCGGCTGGTAGCAG

CTTCGCCAGTTTCCCACGTCTCGCTTTCTACAGGAAGTTTTAGCCTGGGT

TT;

The base sequence of one DNA single strand in the full-length target region of TFPI2 DMR2 is as follows (as set forth in SEQ ID NO: 33):

ATTACTGACACAAACGCTCCCTCAGGGCGTCCCCGTCTGGACTACAG

GAGAAAGTTTGGGAGGCAGGTTCAACTTTTCAACTTGGCGGGGAATTCC

TCTCCCTCTTACACAGTTTGCAGCGCGGGGCGGCGGGGTGACAGTCC

CCGTGCATGAATCAGCCACCCCTCAGGCTCCGCCCCGGCGGGGTCGG

CCGGACGCTCGCCCCGCATAAAGCGGGCACCCGGGCCGCCTGGAGCA

GAAAGCCGCGCACCTCCTCCCGCCAGGCGCTTTCTCGGACGCCTTGCC

CAGCGGGCCGCCCGACCCCCTGCACCATGGACCCCGCTCGCCCCCTG

GGGCTGTCGATTCTGCTGCTTTTCCTGA.

In the above, the detection reagent used in the present example may be any reagent in the art capable of realizing the methylation detection.

Example 4

Figure 2:
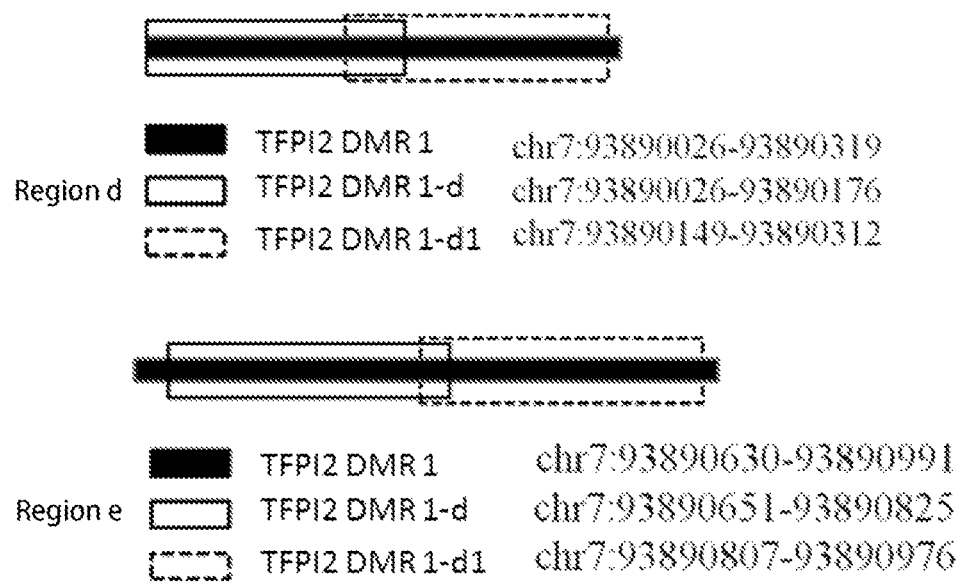
FIG. 2 is a schematic diagram showing the positional relationships of respective target regions of TFPI2 gene in an embodiment of the present disclosure.

The kit for auxiliary diagnosis of colorectal cancer or colorectal adenoma provided in the present example is substantially the same as that in example 2, except that in the present example:

the region d is selected from partial region of TFPI2 DMR1, specifically, referring to FIG. 2, the region d is selected from chr7:93890026-93890176 (named as TFPI2 DMR1-d) and chr7:93890149-93890312 (named as TFPI2 DMR1-d1); and the region e is selected from partial region of TFPI2 DMR2, specifically, referring to FIG. 2, the region e is selected from chr7:93890651-93890825 (named as TFPI2 DMR2-e) and chr7:93890807-93890976 (named as TFPI2 DMR2-e1).

Further, the kit of the present example further contains a primer pair and a fluorescent probe for detecting respective target regions as mentioned above, and the specific sequences are shown in Table 1.

Example 5

The present example provides a method for auxiliary diagnosis of colorectal cancer or colorectal adenoma using the kit of examples 1-4, and the method is as follows.

I. Extraction of DNA template:

(a) When the sample is a tissue sample:

DNA extraction is performed with a DNA extraction kit, e.g. UnigeneDx from Ningbo Youcheng Biomedical Technology Co., Ltd., and as for specific experimental operations, reference can be made to the instructions of the manufacturer.

(b) When the sample is a stool sample, DNA extraction is performed by adopting e.g. a nucleic acid extraction kit from Wuhan Ammunition Life Technology Co., Ltd. (Item No.: AA07), and the operations are as follows:

(1) adding a feces cell lysis solution to 1-5 g of fresh stool sample, mixing the same sufficiently, performing lysis and centrifugation, and then transferring the supernatant to a new clean centrifuge tube.

(2) adding an adsorbent to the supernatant, and performing vortex oscillation to realize sufficient mixing.

(3) performing centrifugation for 2-5 min, and transferring the supernatant to a new centrifuge tube, hereby obtaining a preliminarily treated nucleic acid sample.

(4) adding proteinase K and RNase to the nucleic acid sample obtained after the preliminary treatment, to completely remove protein and RNA.

(5) adding binding buffer CB to the enzyme-treated mixture obtained in the previous step, and obtaining a mixed solution after homogeneous mixing by turning upside down.

(6) adding a prepared gene trapping reagent to the above-mentioned mixed solution, and incubating at room temperature for 1 to 2 hours after homogeneous mixing by turning upside down.

(7) transferring the centrifuge tube to a magnetic shelf after incubation, such that the magnetic beads are magnetized, and discarding the supernatant.

(8) adding rinsing solution WB to resuspend the magnetic beads, and repeatedly washing for 3 times.

(9) adding 750 μL rinsing solution WB to resuspend the magnetic beads, magnetizing the mixture on the magnetic shelf for 2 min and removing the supernatant, and repeatedly washing for 3 times (trying to remove the liquid completely at the last time).

(10) adding 50 μL eluent, mixing the same uniformly through oscillation, incubating the mixture at room temperature for 3-5 min, magnetizing the mixture on the magnetic shelf for 2 min, and transferring the supernatant to a new clean collecting tube, wherein the collected DNA solution is trapped human DNA, which can be preserved at 4° C. or −20° C. for later use and can be used for subsequent genetic detection.

II. Conversion of Sulfite

The nucleic acid conversion kit used is EZ DNA Methylation-Gold™ Kit from ZYMO RESEARCH, and as for specific experimental operations, reference can be made to the instructions of the manufacturer.

III. Fluorescent Quantitative PCR (1) The preparation of PCR reaction solution (the preparation of PCR reaction system) is shown in following Table 2.

TABLE 2

| Main constituents of the kit | |
| --- | --- |
| Composition | Main Constituents |
| PCR reaction solution I | buffer solution, dNTP, primer, probe |
| PCR reaction solution II | hot-start Taq DNA polymerase |
| Positive control | plasmid DNA |

Notes: The primers and the probes in Table 2 are just primers and probes of the kit described in examples 1-4, and corresponding primer pair and probe can be selected according to the target region to be detected. In each PCR reaction, a negative control, a positive control, and a sample to be detected are simultaneously detected.

1) Taking out PCR reaction solution I, PCR reaction solution II, an enzyme, and a positive control, performing oscillation for 30 s after thawing, and then performing instantaneous centrifugation for 30 s to prevent the reagent from remaining on the tube cap;

2) Preparation of the reaction solution: The number of the reaction solution tubes for subpackage is calculated according to the sample quantity for amplification;

20 μL reaction system contains:

| Composition | Volume |
| --- | --- |
| PCR reaction solution I | 19.5 μL |
| PCR reaction solution II | 0.5 μL |

3) Subpackage: the prepared reaction solution is subpackaged into reaction tubes/plates in a volume of 20 μL/tube;

4) Sample addition: treated negative control NC, sample nucleic acid conversion solution, positive control PC, respectively in a volume of 5 μL, are successively added to respective reaction tubes with subpackaged reaction solutions in order. After sample addition, centrifugation is performed briefly for 30 s, after making sure that the tube cap is properly covered or film sealing is realized, and PCR amplification reaction is then performed immediately.

5) As for PCR amplification (PCR amplification and result analysis area), the PCR amplification procedure is set and performed according to Table 3.

TABLE 3

PCR amplification procedure

| | Steps | Temperature | Duration | Cycle Number | Fluorescence Collection |
|---|---|---|---|---|---|
| 1 | Pre-Denaturation | 95° C. | 5 min | 1 | No |
| 2 | Denaturation | 94° C. | 15 s | 45 | |
| 3 | Annealing | 60° C. | 30 s | | Yes |
| 4 | Extension | 72° C. | 30 s | | |
| 5 | Supplementary Extension | 72° C. | 5 min | 1 | |

(2) Result Judgment

The sample detection results can be determined according to the methods in Tables 4-6, after the negative control, the positive control, and the internal control are qualified.

TABLE 4

Method for determining results when detecting a single target region selecting a single target gene

| Gene | Ct-value | Genetic Result Determination |
|---|---|---|
| SDC2 | Ct ≤ 38 | positive SDC2-methylation |
| | Ct > 38 or Unde | negative SDC2-methylation |
| TFPI2 | Ct ≤ 38 | positive TFPI2-methylation |
| | Ct > 38 or Unde | negative TFPI2-methylation |

TABLE 5

Method for determining results when detecting two target regions from two different genes

| Gene Methylation | Determination of Sample Detection Results |
|---|---|
| positive SDC2, positive TFPI2 | positive |
| positive SDC2, negative TFPI2 | |
| negative SDC2, positive TFPI2 | |
| negative SDC2, negative TFPI2 | negative |

TABLE 6

Method for determining detection results when detecting two different target regions from the same gene

| Gene Methylation | Determination of Sample Detection Results |
|---|---|
| positive SDC2 DMR1, negative SDC2 DMR2 | positive |
| negative SDC2 DMR1, positive SDC2 DMR2 | |
| positive SDC2 DMR1, positive SDC2 DMR2 | |

TABLE 6-continued

Method for determining detection results when detecting two different target regions from the same gene

| Gene Methylation | Determination of Sample Detection Results |
|---|---|
| positive SDC2 DMR1, negative SDC2 DMR3 | |
| negative SDC2 DMR1, positive SDC2 DMR3 | |
| positive SDC2 DMR1, positive SDC2 DMR3 | |
| positive SDC2 DMR2, negative SDC2 DMR3 | |
| negative SDC2 DMR2, positive SDC2 DMR3 | |
| positive SDC2 DMR2, positive SDC2 DMR3 | |
| positive TFPI2 DMR1, negative TFPI2 DMR2 | |
| negative TFPI2 DMR1, positive TFPI2 DMR2 | |
| positive TFPI2 DMR1, positive TFPI2 DMR2 | |
| negative SDC2 DMR1, negative SDC2 DMR2 | negative |
| negative SDC2 DMR1, negative SDC2 DMR3 | |
| negative SDC2 DMR2, negative SDC2 DMR3 | |
| negative TFPI2 DMR1, negative TFPI2 DMR2 | |

In the above, sample detection result is positive, representing a relatively higher risk of suffering from colorectal cancer or colorectal adenoma, and it is recommended that the subject to be detected has a colonoscopy to make a definite diagnosis; and sample detection result is negative, which cannot completely exclude the possibility that the subject to be detected suffers from colorectal cancer or colorectal adenoma.

Experimental Example 1

Methylation of different detection regions of SDC2 gene, i.e. SDC2 DMR1, SDC2 DMR2, and SDC2 DMR3, is separately detected, and the differences in colorectal cancer diagnosis effects of individual detection regions and combinations of any two detection regions are compared.

Enrolled samples: (1) 302 tissue samples with known clinical diagnosis results, including 144 samples of colorectal cancer, 104 samples of adenoma, and 54 normal samples; and (2) 584 stool samples with known clinical diagnosis results, including 252 samples of cancer, 146 samples of adenoma, and 186 normal samples. Information about enrolled samples is shown in following Table 7.

TABLE 7

Clinical information of tissue samples and stool samples

| | Sex | Cancer | Adenoma | Normal |
|---|---|---|---|---|
| Tissue Sample | Male | 82 | 56 | 32 |
| | Female | 62 | 48 | 22 |
| | Median Age (Range) | 63 (30-90) | 61 (33-87) | 59 (32-84) |
| Stool Sample | Male | 140 | 85 | 100 |
| | Female | 112 | 61 | 86 |
| | Median Age (Range) | 60 (22-81) | 58 (25-84) | 59 (30-83) |

Method: Detection is performed using the kit provided in example 2 and adopting the method provided in example 5, wherein specific primer pairs used for detecting SDC2 DMR1, SDC2 DMR2 and SDC2 DMR3 are respectively primer pair a, primer pair b1, and primer pair c1, and the fluorescent group and the quenching group of probe a are FAM and MGB-NFQ, the fluorescent group and the quenching group of probe b are ROX and MGB-NFQ, and the fluorescent group and the quenching group of probe c1 are VIC and MGB-NFQ.

The detection sensitivity and specificity of each DMR and combinations of respective two DMRs are shown in following Table 8:

TABLE 8

Detection effects of different SDC2 DMRs in tissue samples and stool samples

| Sample Type | Detection Target Region | Sensitivity to Cancer | Sensitivity to Adenoma | Specificity | AUC1 (cancer) | AUC2 (adenoma) |
|---|---|---|---|---|---|---|
| Tissue Sample | SDC2 DMR 1-a | 88.7% | 70.2% | 96.3% | 0.979 | 0.841 |
| | SDC2 DMR 2-b1 | 90.1% | 71.2% | 98.1% | 0.976 | 0.856 |
| | SDC2 DMR 3-c1 | 90.8% | 72.1% | 98.1% | 0.980 | 0.891 |
| | SDC2 DMR 1-a + SDC2 DMR 2-b1 | 93.0% | 74.0% | 96.3% | 0.981 | 0.910 |
| | SDC2 DMR 1-a + SDC2 DMR 3-c1 | 95.8% | 78.8% | 96.3% | 0.985 | 0.926 |
| | SDC2 DMR 2-b1 + SDC2 DMR 3-c1 | 94.4% | 77.9% | 96.3% | 0.984 | 0.914 |
| Stool Sample | SDC2 DMR 1-a | 88.5% | 69.2% | 97.3% | 0.856 | 0.773 |
| | SDC2 DMR 2-b1 | 89.7% | 71.9% | 97.8% | 0.891 | 0.787 |
| | SDC2 DMR 3-c1 | 91.7% | 73.3% | 98.4% | 0.914 | 0.804 |
| | SDC2 DMR 1-a + SDC2 DMR 2-b1 | 90.1% | 72.6% | 97.3% | 0.923 | 0.807 |
| | SDC2 DMR 1-a + SDC2 DMR 3-c1 | 94.0% | 79.5% | 97.3% | 0.935 | 0.83 |
| | SDC2 DMR 2-b1 + SDC2 DMR 3-c1 | 93.3% | 76.0% | 97.3% | 0.933 | 0.816 |

It can be seen from Table 8: as for the detection of tissue samples, when a single detection region is detected as target region, the detection sensitivity and specificity of the three DMRs of the SDC2 gene to samples of cancer and samples of adenoma are respectively 88.7% and 70.2%, 90.1% and 71.2%, and 90.8% and 72.1%, of which SDC2 DMR3 has the best detection sensitivity and specificity; when two detection regions are detected as target region, the detection sensitivity of the combination of SDC2 DMR 1-a+SDC2 DMR 2-b1 to two samples are respectively 93.0% and 74.0%, the sensitivity and the specificity of the combination of SDC2 DMR 1-a+SDC2 DMR 3-c1 are respectively 95.8% and 78.8%, and the sensitivity and the specificity of the combination of SDC2 DMR 2-b1+SDC2 DMR 3-c1 are respectively 94.4% and 77.9%, wherein the sensitivity and the specificity of the combination of SDC2 DMR 1-a+SDC2 DMR 3-c1 are both relatively better.

The detection results of stool samples are substantially identical with that of tissue samples: when a single detection region is detected as target region, the detection sensitivity and specificity of SDC2 DMR 3-c1 are both relatively better; and when two detection regions are detected as target region, the sensitivity and the specificity of the combination of SDC2 DMR 1-a+SDC2 DMR 3-c1 are both relatively better.

Experimental Example 2

Methylation of different detection regions of TFPI2 gene, i.e. TFPI2 DMR1 and TFPI2 DMR2, is respectively detected, and the differences in colorectal cancer diagnosis effects of individual detection regions and the combination of both detection regions are compared:

Enrolled samples: (1) 302 tissue samples with known clinical diagnosis results, including 144 samples of colorectal cancer, 104 samples of adenoma, and 54 normal samples. (2) 584 stool samples with known clinical diagnosis results, including 252 samples of cancer, 146 samples of adenoma, and 186 normal samples, and information about enrolled samples is shown in Table 7 in the part of experimental examples.

Method: Detection is performed using the kit provided in example 4 and adopting the method provided in example 5, wherein specific primer pairs used for detecting TFPI2 DMR1 and TFPI2 DMR2 are respectively primer pair d1 and primer pair e1, and the fluorescent group and the quenching group of probe d1 are FAM and MGB-NFQ, and the fluorescent group and the quenching group of probe e1 are ROX and MGB-NFQ, and the detection sensitivity and specificity of each DMR and the combination of both DMRs are shown in following Table 9.

TABLE 9

Detection effects of different TFPI2 DMRs in tissue samples and stool samples

| Sample Type | Detection Target Region | Sensitivity to Cancer | Sensitivity to Adenoma | Specificity | AUC1 (cancer) | AUC2 (adenoma) |
|---|---|---|---|---|---|---|
| Tissue Sample | TFPI 2 DMR 1-d1 | 90.1% | 69.2% | 96.3% | 0.965 | 0.876 |
| | TFPI2 DMR2-e1 | 88.0% | 68.3% | 96.3% | 0.955 | 0.819 |
| | TFPI 2 DMR 1-d1 + TFPI2 DMR2-e1 | 92.3% | 74.0% | 96.3% | 0.973 | 0.882 |

TABLE 9-continued

Detection effects of different TFPI2 DMRs in tissue samples and stool samples

| Sample Type | Detection Target Region | Sensitivity to Cancer | Sensitivity to Adenoma | Specificity | AUC1 (cancer) | AUC2 (adenoma) |
|---|---|---|---|---|---|---|
| Stool Sample | TFPI 2 DMR 1-d1 | 90.9% | 71.9% | 96.8% | 0.937 | 0.827 |
| | TFPI2 DMR2-e1 | 90.1% | 70.5% | 96.8% | 0.922 | 0.815 |
| | TFPI 2 DMR 1-d1 + TFPI2 DMR2-e1 | 93.3% | 76.0% | 96.2% | 0.945 | 0.833 |

It can be seen from Table 9: in tissue samples, the detection sensitivities of TFPI 2 DMR 1-d1 to samples of cancer and to samples of adenoma are respectively 90.1% and 69.2%, the detection sensitivity and specificity of TFPI2 DMR2-e1 to samples of cancer are respectively 88.0% and 68.3%, wherein the detection sensitivity of TFPI 2 DMR 1-d1 is better than that of TFPI2 DMR2-e1; the sensitivities of the combination of TFPI 2 DMR 1-d1+TFPI2 DMR2-e1 are respectively 92.3% and 74.0%, and the detection sensitivity of the combination of two DMRs is higher than that of individual DMR; and the detection results of TFPI 2 DMR 1-d1 and TFPI2 DMR2-e1 in stool samples are identical with that in tissue samples.

Experimental Example 3

Any one region of the three detection regions on the SDC2 gene is combined with any one detection region of the two detection regions on the TFPI2 gene, and the differences of different combinations in the colorectal cancer diagnosis effects are compared:

Enrolled samples: 584 stool samples with known clinical diagnosis results, including 252 samples of cancer, 146 samples of adenoma, and 186 normal samples, and information about enrolled samples is shown in Table 7 in experimental examples.

Method: Detection is performed using the kits provided in examples 2 and 4 and adopting the method provided in example 5, wherein specific primer pairs used for detecting SDC2 DMR1, SDC2 DMR2 and SDC2 DMR3 are respectively primer pair a, primer pair b1, and primer pair c1, specific primer pairs used for detecting TFPI2 DMR1 and TFPI2 DMR2 are respectively primer pair d1 and primer pair e1, and the detection sensitivity and specificity of each DMR and combinations of two DMRs are shown in Table 10. In the above, in all the six combinations, FAM is used as fluorescent reporter group of probes of the SDC2 gene, while MGB-NFQ is used as quenching group; and ROX is used as fluorescent reporter group of probes of the TFPI2 gene, while MGB-NFQ is used as quenching group.

TABLE 10

Detection effects of different DMR combinations of SDC2 and TFPI2 in stool samples

| Region Name | Sensitivity to Cancer | Sensitivity to Adenoma | Specificity | AUC1 (cancer) | AUC2 (adenoma) |
|---|---|---|---|---|---|
| SDC2 DMR 1-a + TFPI2 DMR 1-d1 | 93.3% | 74.0% | 96.8% | 0.985 | 0.892 |
| SDC2 DMR 1-a + TFPI2 DMR 2-e1 | 90.9% | 73.3% | 96.2% | 0.967 | 0.845 |
| SDC2 DMR 2-b1 + TFPI2 DMR 1-d1 | 92.9% | 74.7% | 96.8% | 0.976 | 0.865 |
| SDC2 DMR 2-b1 + TFPI2 DMR 2-e1 | 92.9% | 75.3% | 96.2% | 0.943 | 0.833 |
| SDC2 DMR 3-c1 + TFPI2 DMR 1-d1 | 94.8% | 78.8% | 96.2% | 0.992 | 0.898 |
| SDC2 DMR 3-c1 + TFPI2 DMR 2-e1 | 93.7% | 76.7% | 96.2% | 0.954 | 0.841 |

It can be seen from Table 10: Relatively higher sensitivity and specificity are achieved, when any one DMR of SDC2 and any one DMR of TFPI2 are used in combination, especially when the primer pair c1 of SDC2 is used in combination with the primer pair d1 of TFPI2, the best sensitivity and specificity are achieved, wherein the detection sensitivity to cancer is 94.8%, the detection sensitivity in samples of adenoma is 78.8% and the specificity is 96.2%, and AUC respectively reaches 0.992 and 0.898.

Experimental Example 4

Comparison of the Diagnosis Effect of the Case where the Diagnostic Method of Example 5 of the Present Disclosure is Adopted with that of the Control Group (1) Control group: Methylation situations of two regions, i.e. chr8:96494146-96494214 of SDC2 gene and chr7: 98890723-98890795 of TFPI2 gene, are detected, combined diagnosis of colorectal cancer is realized according to the results, and as for the judgement method, reference can be made to example 5.

Sequences of control primer pairs and probes for composite detection of methylation of other regions of the SDC2 gene and the TFPI2 gene are as follows:

Primer pairs for detecting methylation of the region chr8:96494146-96494214 of the SDC2 gene:

SDC2-F10: GTTTGAGTCGTAATCGTTGC
(as set forth in SEQ ID NO: 34);
and

SDC2-R10: TCCTACCCAACGCTCGACG
(as set forth in SEQ ID NO: 35).

Probe for detecting methylation of the region chr8: 96494146-96494214 of the SDC2 gene:

SDC2-P5: CGGATTCGTGTGCGC
(as set forth in SEQ ID NO: 36).

Primer pairs for detecting methylation of the region chr7:98890723-98890795 of the TFPI2 gene:

TFPI2-F6: ACGTTCGTTTCGTATAAAGC (as set forth in SEQ ID NO: 37);
and

TFPI2-R4: ACGCCTAACGAAAAAAAATACG
(as set forth in SEQ ID NO: 38).

Probe for detecting methylation of the region chr7: 98890723-98890795 of the TFPI2 gene:

TFPI2-P2: CTCCAAACGACCCG
(as set forth in SEQ ID NO: 39).

(2) Enrolled samples: 150 stool samples with known clinical diagnosis results, including 50 samples of cancer, 50 samples of adenoma, and 50 normal samples. Information about enrolled samples is shown in Table 11.

TABLE 11

Clinical information about 150 stool samples

|  | Sex | Cancer | Adenoma | Normal |
|---|---|---|---|---|
| Stool Sample | Male | 28 | 25 | 29 |
|  | Female | 22 | 25 | 21 |
|  | Median Age (Range) | 57 (22-78) | 60 (23-85) | 59 (29-83) |

Method: Detection is performed adopting the method of example 5, wherein specific primer pairs used for detecting SDC2 DMR1, SDC2 DMR2, and SDC2 DMR3 are respectively primer pair a, primer pair b1, and primer pair c1, specific primer pairs used for detecting TFPI2 DMR1 and TFPI2 DMR2 are respectively primer pair d1 and primer pair e1, and the detection sensitivity and specificity obtained for each case are shown in Table 12. In Table 12, the fluorescent reporter groups of probes a, b, and c1 in the first three combinations are respectively FAM, ROX, and VIC; the fluorescent reporter groups of probes d1 and e1 in the fourth combination are respectively FAM and TOX; in all the combinations 5-10, FAM is used as fluorescent group of the probes of the SDC2 gene; ROX is used as fluorescent group of the probes of the TFPI2 gene; and in combinations 1-10, MGB-NFQ is used as quenching gene for all probes.

TABLE 12

Comparison results between the present disclosure and the prior art

| Target Region Name | Sensitivity to Cancer | Sensitivity to Adenoma | Specificity | AUC1 (cancer) | AUC2 (adenoma) |
|---|---|---|---|---|---|
| SDC2 DMR 1-a + SDC2 DMR 2-b1 | 94% | 80% | 96% | 0.959 | 0.857 |
| SDC2 DMR 1-a + SDC2 DMR 3-c1 | 98% | 84% | 98% | 0.994 | 0.887 |
| SDC2 DMR 2-b1 + SDC2 DMR 3-c1 | 94% | 82% | 96% | 0.951 | 0.846 |
| TFPI2 DMR 1-d1 + TFPI2 DMR 2-e1 | 96% | 82% | 96% | 0.986 | 0.831 |
| SDC2 DMR 1-a + TFPI2 DMR 1-d1 | 94% | 82% | 98% | 0.952 | 0.854 |
| SDC2 DMR 1-a + TFPI2 DMR 2-e1 | 94% | 78% | 98% | 0.939 | 0.827 |
| SDC2 DMR 2-b1 + TFPI2 DMR 1-d1 | 96% | 82% | 94% | 0.979 | 0.819 |
| SDC2 DMR 2-b1 + TFPI2 DMR 2-e1 | 96% | 82% | 98% | 0.958 | 0.861 |
| SDC2 DMR 3-c1 + TFPI2 DMR 1-d1 | 98% | 84% | 98% | 0.996 | 0.894 |

TABLE 12-continued

Comparison results between the present disclosure and the prior art

| Target Region Name | Sensitivity to Cancer | Sensitivity to Adenoma | Specificity | AUC1 (cancer) | AUC2 (adenoma) |
|---|---|---|---|---|---|
| SDC2 DMR 3-c1 + TFPI2 DMR 2-e1 | 98% | 82% | 98% | 0.989 | 0.875 |
| SDC2-F10/SDC2-R10 + TFPI2-F6/TFPI2-R4 | 86% | 80% | 96% | 0.911 | 0.830 |

This shows that the sensitivity to cancer of the target regions detected by the kit of the embodiments of the present disclosure is much higher than that of the target regions of the control group.

Experimental Example 6

Diagnosis effects of detection of amplified target regions using different primer pairs in Table 1

Enrolled samples: 60 stool samples with known clinical diagnosis results, including 20 samples from subjects suffering from cancer, 20 samples from subjects suffering from adenoma, and 20 samples from normal subjects.

Information about enrolled samples is shown in Table 13.

TABLE 13

Clinical information about 60 stool samples

| | Sex | Cancer | Adenoma | Normal |
|---|---|---|---|---|
| Stool Sample | Male | 10 | 10 | 10 |
| | Female | 10 | 10 | 10 |
| | Median Age (Range) | 55 (24-70) | 52 (27-68) | 59 (31-73) |

Method: Detection is performed adopting the method of example 5, wherein the fluorescent reporter groups of probes a, b, c, c1, d, d1, e, and e are respectively FAM, ROX, VIC, VIC, FAM, FAM, ROX, and ROX, and MGB-NFQ is used as fluorescent quenching group for all the probes. The detection sensitivity and specificity obtained for each primer pair are shown in Table 14.

TABLE 14

Detection results of different primer pairs for respective DMRs of SDC2 and TFPI2

| Primer Pair | Target Region | Sensitivity To Cancer | Sensitivity To Adenoma | Specificity | AUC1 (cancer) | AUC2 (adenoma) |
|---|---|---|---|---|---|---|
| a | SDC2 DMR 1-a | 100% | 90% | 100% | 0.967 | 0.856 |
| a1 | SDC2 DMR 1-a1 | 100% | 80% | 100% | 0.952 | 0.841 |
| b | SDC2 DMR 2-b | 100% | 80% | 100% | 0.942 | 0.798 |
| b1 | SDC2 DMR 2-b1 | 100% | 90% | 100% | 0.956 | 0.823 |
| c | SDC2 DMR 3-c | 100% | 90% | 90% | 0.992 | 0.869 |
| c1 | SDC2 DMR 3-c1 | 100% | 90% | 100% | 0.999 | 0.882 |
| d | TFPI2 DMR 1-d | 100% | 80% | 100% | 0.963 | 0.819 |
| d1 | TFPI2 DMR 1-d1 | 100% | 90% | 100% | 0.995 | 0.843 |
| e | TFPI2 DMR 2-e | 100% | 80% | 100% | 0.921 | 0.805 |
| e1 | TFPI2 DMR 2-e1 | 100% | 90% | 100% | 0.937 | 0.842 |

According to the sensitivity, specificity, and AUG values obtained in Table 14, it can be seen that relatively better primer pairs for amplifying SDC2 DMR1, SDC2 DMR2, SDC2 DMR3, TFPI2 DMR1, and TFPI2 DMR2 are respectively primer pair a, primer pair b1, primer pair c1, primer pair d1, and primer pair e1.

The above mentioned are merely preferred embodiments of the present disclosure, and not intended to limit the present disclosure, and for a person skilled in the art, the present disclosure may be modified and changed in various ways. Any modifications, equivalent substitutions and improvements made within the spirit and principle of the present disclosure shall all be covered in the scope of protection of the present disclosure.

INDUSTRIAL APPLICABILITY

As for the kit and the method of the present disclosure, the sensitivity and the specificity of detection of colorectal cancer can be significantly improved by using different detection regions of same or different colorectal cancer-related genes as detection target region of methylation, so as to realize the purpose of early, rapid and accurate detection of colorectal cancer and colorectal adenoma.

The invention claimed is:

1. A kit for auxiliary diagnosis of colorectal cancer, comprising a detection reagent for detecting methylation of a colorectal cancer-related gene; the colorectal cancer-related gene is one selected from the group consisting of SDC2 gene, TFPI2 gene and a combination thereof; the detection reagent contains a first reagent for detecting methylation of a first target region on the SDC2 gene or/and a second reagent for detecting methylation of a second target region on the TFPI2 gene,
   wherein the first target region is a region c,
   wherein the region c is selected from a full-length region and a partial region of chr8:96494006-96494335; and the second target region is a region d,
   wherein the region d is selected from a full-length region and a partial region of chr7:93890026-93890319,
   wherein the first reagent contains a first nucleic acid group for detecting methylation of the first target region, and the first nucleic acid group contains a combination of a fluorescent probe c and a primer pair c or a combination of a fluorescent probe c1 and a primer pair c1;
   the second reagent contains a second nucleic acid group for detecting methylation of the second target region, and the second nucleic acid group contains a combination of a primer pair d and a fluorescent probe d or a combination of a primer pair d1 and a fluorescent probe d1;
   wherein base sequences of the primer pair c consist of nucleotide sequences of SEQ ID NOs: 11-12, and a base sequence of the fluorescent probe c consists of a nucleotide sequence of SEQ ID NO: 13; and base sequences of the primer pair c1 consist of nucleotide sequences of SEQ ID NOs: 14-15, and a base sequence of the fluorescent probe c1 consists of a nucleotide sequence of SEQ ID NO: 16; and
   base sequences of the primer pair d consist of nucleotide sequences of SEQ ID NOs: 17-18, and a base sequence of the fluorescent probe d consists of a nucleotide sequence of SEQ ID NO: 19; and base sequences of the primer pair d1 consist of nucleotide sequences of SEQ ID NOs: 20-21, and a base sequence of the fluorescent probe d1 consists of a nucleotide sequence of SEQ ID NO: 22.

2. The kit for auxiliary diagnosis of colorectal cancer according to claim 1, wherein the kit for auxiliary diagnosis of colorectal cancer further contains one or more of following: sulfites, sample preservation solutions, nucleic acid extraction solutions, PCR reaction liquids, positive control, negative control, endogenous reference, and standard reagents.

3. The kit for auxiliary diagnosis of colorectal cancer according to claim 1, wherein a detection sample of the kit is a blood sample, a colorectal tissue sample or a stool sample taken from a subject to be detected.

* * * * *

SEQUENCE LISTING

<160> NUMBER OF SEQ ID NOS: 39

<210> SEQ ID NO 1
<211> LENGTH: 25
<212> TYPE: DNA
<213> ORGANISM: Artificial sequence
<220> FEATURE:
<223> OTHER INFORMATION: Forward Primer in pair a

<400> SEQUENCE: 1
ttagaaaagg gaaagtgaag aaggg                                          25

<210> SEQ ID NO 2
<211> LENGTH: 22
<212> TYPE: DNA
<213> ORGANISM: Artificial sequence
<220> FEATURE:
<223> OTHER INFORMATION: Reverse Primer in pair a

<400> SEQUENCE: 2
caactccgaa aaccaataaa cg                                             22

<210> SEQ ID NO 3
<211> LENGTH: 25
<212> TYPE: DNA
<213> ORGANISM: Artificial sequence
<220> FEATURE:
<223> OTHER INFORMATION: Forward Primer in pair a1

<400> SEQUENCE: 3
agagaggaaa agtggggaga gaaag                                          25

<210> SEQ ID NO 4
<211> LENGTH: 25
<212> TYPE: DNA
<213> ORGANISM: Artificial sequence
<220> FEATURE:
<223> OTHER INFORMATION: Reverse Primer in pair a1

<400> SEQUENCE: 4
tcccaaataa acccgaaaaa aattc                                          25

<210> SEQ ID NO 5
<211> LENGTH: 26
<212> TYPE: DNA
<213> ORGANISM: Artificial sequence
<220> FEATURE:
<223> OTHER INFORMATION: Probe a

<400> SEQUENCE: 5
ctataactac gccgactcta ctcacc                                         26

<210> SEQ ID NO 6
<211> LENGTH: 25
<212> TYPE: DNA
<213> ORGANISM: Artificial sequence
<220> FEATURE:
<223> OTHER INFORMATION: Forward Primer in pair b

<400> SEQUENCE: 6
agaggaaaag aagaggagga gaagg                                          25

<210> SEQ ID NO 7
<211> LENGTH: 19
<212> TYPE: DNA
<213> ORGANISM: Artificial sequence

```
<220> FEATURE:
<223> OTHER INFORMATION: Reverse Primer in pair b

<400> SEQUENCE: 7
acgacgaaaa cgcgcgatc                                                  19

<210> SEQ ID NO 8
<211> LENGTH: 22
<212> TYPE: DNA
<213> ORGANISM: Artificial sequence
<220> FEATURE:
<223> OTHER INFORMATION: Forward Primer in pair b1

<400> SEQUENCE: 8
gtagtcgcgg agttagtggt tt                                              22

<210> SEQ ID NO 9
<211> LENGTH: 25
<212> TYPE: DNA
<213> ORGANISM: Artificial sequence
<220> FEATURE:
<223> OTHER INFORMATION: Reverse Primer in pair b1

<400> SEQUENCE: 9
cgctaactta aaaaaaaact acgac                                           25

<210> SEQ ID NO 10
<211> LENGTH: 20
<212> TYPE: DNA
<213> ORGANISM: Artificial sequence
<220> FEATURE:
<223> OTHER INFORMATION: Probe b

<400> SEQUENCE: 10
atctaaaaaa caacgcgtcc                                                 20

<210> SEQ ID NO 11
<211> LENGTH: 25
<212> TYPE: DNA
<213> ORGANISM: Artificial sequence
<220> FEATURE:
<223> OTHER INFORMATION: Forward Primer in pair c

<400> SEQUENCE: 11
gagtattaat ttcgtgtcgg gagtg                                           25

<210> SEQ ID NO 12
<211> LENGTH: 24
<212> TYPE: DNA
<213> ORGANISM: Artificial sequence
<220> FEATURE:
<223> OTHER INFORMATION: Reverse Primer in pair c

<400> SEQUENCE: 12
taccgcaacg attacgactc aaac                                            24

<210> SEQ ID NO 13
<211> LENGTH: 20
<212> TYPE: DNA
<213> ORGANISM: Artificial sequence
<220> FEATURE:
<223> OTHER INFORMATION: Probe c

<400> SEQUENCE: 13
caactacgcc ccgaaaacgc                                                 20
```

```
<210> SEQ ID NO 14
<211> LENGTH: 23
<212> TYPE: DNA
<213> ORGANISM: Artificial sequence
<220> FEATURE:
<223> OTHER INFORMATION: Forward Primer in pair c1

<400> SEQUENCE: 14
cgagtttgag tcgtaatcgt tgc                                              23

<210> SEQ ID NO 15
<211> LENGTH: 26
<212> TYPE: DNA
<213> ORGANISM: Artificial sequence
<220> FEATURE:
<223> OTHER INFORMATION: Reverse Primer in pair c1

<400> SEQUENCE: 15
tccgccgaca cgcaaaccac caaacc                                           26

<210> SEQ ID NO 16
<211> LENGTH: 25
<212> TYPE: DNA
<213> ORGANISM: Artificial sequence
<220> FEATURE:
<223> OTHER INFORMATION: Probe c1

<400> SEQUENCE: 16
aacaaaacga aacctcctac ccaac                                            25

<210> SEQ ID NO 17
<211> LENGTH: 21
<212> TYPE: DNA
<213> ORGANISM: Artificial sequence
<220> FEATURE:
<223> OTHER INFORMATION: Forward Primer in pair d

<400> SEQUENCE: 17
atttgggagg tttgcgacga t                                                21

<210> SEQ ID NO 18
<211> LENGTH: 20
<212> TYPE: DNA
<213> ORGANISM: Artificial sequence
<220> FEATURE:
<223> OTHER INFORMATION: Reverse Primer in pair d

<400> SEQUENCE: 18
aaacccaaac taaaacttcc                                                  20

<210> SEQ ID NO 19
<211> LENGTH: 25
<212> TYPE: DNA
<213> ORGANISM: Artificial sequence
<220> FEATURE:
<223> OTHER INFORMATION: Probe d

<400> SEQUENCE: 19
cgaaaatcct aaatacgcgc aaaac                                            25

<210> SEQ ID NO 20
<211> LENGTH: 20
<212> TYPE: DNA
<213> ORGANISM: Artificial sequence
<220> FEATURE:
<223> OTHER INFORMATION: Forward Primer in pair d1
```

```
<400> SEQUENCE: 20
cgcggagatt tgttttttgt                                              20

<210> SEQ ID NO 21
<211> LENGTH: 22
<212> TYPE: DNA
<213> ORGANISM: Artificial sequence
<220> FEATURE:
<223> OTHER INFORMATION: Reverse Primer in pair d1

<400> SEQUENCE: 21
aacaaacatc gtcgcaaacc tc                                           22

<210> SEQ ID NO 22
<211> LENGTH: 20
<212> TYPE: DNA
<213> ORGANISM: Artificial sequence
<220> FEATURE:
<223> OTHER INFORMATION: Probe d1

<400> SEQUENCE: 22
ataaaacccg acaaaatccg                                              20

<210> SEQ ID NO 23
<211> LENGTH: 19
<212> TYPE: DNA
<213> ORGANISM: Artificial sequence
<220> FEATURE:
<223> OTHER INFORMATION: Forward Primer in pair e

<400> SEQUENCE: 23
ttaggtttcg tttcggcgg                                               19

<210> SEQ ID NO 24
<211> LENGTH: 25
<212> TYPE: DNA
<213> ORGANISM: Artificial sequence
<220> FEATURE:
<223> OTHER INFORMATION: Reverse Primer in pair e

<400> SEQUENCE: 24
acaaccccaa aaaacgaacg aaatc                                        25

<210> SEQ ID NO 25
<211> LENGTH: 24
<212> TYPE: DNA
<213> ORGANISM: Artificial sequence
<220> FEATURE:
<223> OTHER INFORMATION: Probe e

<400> SEQUENCE: 25
tctactccaa acgacccgaa tacc                                         24

<210> SEQ ID NO 26
<211> LENGTH: 25
<212> TYPE: DNA
<213> ORGANISM: Artificial sequence
<220> FEATURE:
<223> OTHER INFORMATION: Forward Primer in pair e1

<400> SEQUENCE: 26 gttttttag ggcgttttcg tttgg                                         25

<210> SEQ ID NO 27
```

```
<211> LENGTH: 21
<212> TYPE: DNA
<213> ORGANISM: Artificial sequence
<220> FEATURE:
<223> OTHER INFORMATION: Reverse Primer in pair e1

<400> SEQUENCE: 27
ccgccgaaac gaaacctaaa a                                              21

<210> SEQ ID NO 28
<211> LENGTH: 25
<212> TYPE: DNA
<213> ORGANISM: Artificial sequence
<220> FEATURE:
<223> OTHER INFORMATION: Probe e1

<400> SEQUENCE: 28
ttcatacacg aaaactatca ccccg                                          25

<210> SEQ ID NO 29
<211> LENGTH: 285
<212> TYPE: DNA
<213> ORGANISM: Homo sapiens

<400> SEQUENCE: 29
agaaaagcta catacgtctc tcgtttcttc actaattgtt ctctagaaaa gggaaagtga    60
agaagggaaa gagaaaagac aacggggaag aaaagagcat agaggagaga ggaaagtgg    120 ggagagaaag gaagaaaagg actgagaaaa cgcaggagcc ctggcttgcc ggtgagcaga   180
gccggcgcag ccacagcgcg gagccgcggc gcccactggt cctcggagct gccaatcggc   240
gtgtaatcct gtaggaattt ctcccgggtt tatctgggag tcaca                   285

<210> SEQ ID NO 30
<211> LENGTH: 235
<212> TYPE: DNA
<213> ORGANISM: Homo sapiens

<400> SEQUENCE: 30
agaggaaaag aagaggagga gaaggaggag gacccgggga gggaggcgcg gcgcgggagg    60
aggaggggcg cagccgcgga gccagtggcc ccgcttggac gcgctgctct ccagataccc   120
ccggagctcc agccgcgcgg atcgcgcgct cccgccgctc tgcccctaaa cttctgccgt   180
agctcccttt caagccagcg aatttattcc ttaaaaccag aaactgaacc tcggc        235

<210> SEQ ID NO 31
<211> LENGTH: 330
<212> TYPE: DNA
<213> ORGANISM: Homo sapiens

<400> SEQUENCE: 31
gagcaccaac tccgtgtcgg gagtgcagaa accaacaagt gagagggcgc cgcgttcccg    60
gggcgcagct gcgggcggcg ggagcaggcg caggaggagg aagcgagcgc ccccgagccc   120
cgagcccgag tccccgagcc tgagccgcaa tcgctgcggt actctgctcc ggattcgtgt   180
gcgcgggctg cgccgagcgc tgggcaggag gcttcgtttt gccctggttg caagcagcgg   240
ctgggagcag ccggtccctg gggaatatgc ggcgcgcgtg gatcctgctc accttgggct   300
tggtggcctg cgtgtcggcg gagtcggtga                                    330

<210> SEQ ID NO 32
<211> LENGTH: 294
```

```
<212> TYPE: DNA
<213> ORGANISM: Homo sapiens

<400> SEQUENCE: 32
gaaataacgc ggagatctgt ctcctgcccc tagactacgg accctgccgg gccctacttc    60
tccgttacta ctacgacagg tacacgcaga gctgccgcca gttcctgtac gggggctgcg   120
agggcaacgc caacaatttc tacacctggg aggcttgcga cgatgcttgc tggaggatag   180
aaagtaagtg ccctgcgcgc acccaggact ctcgcgctcc ttgcgccggc ggctggtagc   240
agcttcgcca gtttcccacg tctcgctttc tacaggaagt tttagcctgg gttt         294

<210> SEQ ID NO 33
<211> LENGTH: 362
<212> TYPE: DNA
<213> ORGANISM: Homo sapiens

<400> SEQUENCE: 33
attactgaca caaacgctcc ctcagggcgt ccccgtctgg actacaggag aaagtttggg    60
aggcaggttc aacttttcaa cttggcgggg aattcctctc cctcttacac agtttgcagc   120 gcggggggcgg cggggtgaca gtccccgtgc atgaatcagc caccctcag gctccgcccc    180 ggcgggggtc ggccggacgc tcgccccgca taaagcgggc acccgggccg cctggagcag   240
aaagccgcgc acctcctccc gccaggcgct ttctcggacg ccttgcccag cgggccgccc   300
gaccccctgc accatggacc ccgctcgccc cctggggctg tcgattctgc tgcttttcct   360
ga                                                                  362

<210> SEQ ID NO 34
<211> LENGTH: 20
<212> TYPE: DNA
<213> ORGANISM: Artificial sequence
<220> FEATURE:
<223> OTHER INFORMATION: Forward primer for detecting methylation of the
      region chr8:96494146-96494214 of the SDC2 gene

<400> SEQUENCE: 34
gtttgagtcg taatcgttgc                                                20

<210> SEQ ID NO 35
<211> LENGTH: 19
<212> TYPE: DNA
<213> ORGANISM: Artificial sequence
<220> FEATURE:
<223> OTHER INFORMATION: Reverse primer for detecting methylation of the
      region chr8:96494146-96494214 of the SDC2 gene

<400> SEQUENCE: 35
tcctacccaa cgctcgacg                                                 19

<210> SEQ ID NO 36
<211> LENGTH: 15
<212> TYPE: DNA
<213> ORGANISM: Artificial sequence
<220> FEATURE:
<223> OTHER INFORMATION: Probe for detecting methylation of the region
      chr8:96494146-96494214 of the SDC2 gene

<400> SEQUENCE: 36
cggattcgtg tgcgc                                                     15

<210> SEQ ID NO 37
<211> LENGTH: 20
```

```
<212> TYPE: DNA
<213> ORGANISM: Artificial sequence
<220> FEATURE:
<223> OTHER INFORMATION: Forward primer for detecting methylation of the
      region chr7:98890723-98890795 of the TFPI2 gene

<400> SEQUENCE: 37
acgttcgttt cgtataaagc                                              20

<210> SEQ ID NO 38
<211> LENGTH: 22
<212> TYPE: DNA
<213> ORGANISM: Artificial sequence
<220> FEATURE:
<223> OTHER INFORMATION: Reverse primer for detecting methylation of the
      region chr7:98890723-98890795 of the TFPI2 gene

<400> SEQUENCE: 38
acgcctaacg aaaaaaaata cg                                           22

<210> SEQ ID NO 39
<211> LENGTH: 14
<212> TYPE: DNA
<213> ORGANISM: Artificial sequence
<220> FEATURE:
<223> OTHER INFORMATION: Probe for detecting methylation of the region
      chr7:98890723-98890795 of the TFPI2 gene

<400> SEQUENCE: 39
ctccaaacga cccg                                                    14
```